United States Patent
Schloesser et al.

[11] Patent Number: 5,990,327
[45] Date of Patent: *Nov. 23, 1999

[54] USE OF AMINOTRIARYLMETHANES FOR MARKING HYDROCARBONS AND NOVEL AMINOTRIARYLMETHANES

[75] Inventors: Ulrike Schloesser; Karin Heidrun Beck, both of Ludwigshafen, Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/549,763
[22] PCT Filed: Jun. 15, 1994
[86] PCT No.: PCT/EP94/01941
  § 371 Date: Nov. 30, 1995
  § 102(e) Date: Nov. 30, 1995
[87] PCT Pub. No.: WO95/00606
  PCT Pub. Date: Jan. 5, 1995

[30] Foreign Application Priority Data

Jun. 21, 1993 [DE] Germany .............. 43 20 456

[51] Int. Cl.⁶ .............. C09B 11/00; C07C 7/20
[52] U.S. Cl. .............. 552/100; 585/2; 585/3; 585/4
[58] Field of Search .............. 552/104; 548/345.1; 585/2, 3, 4

[56] References Cited

U.S. PATENT DOCUMENTS 5,145,573  9/1992  Riedel et al. .............. 208/14
5,233,048  8/1993  Eckstein et al. .............. 548/345.1

*Primary Examiner*—S. Mark Clardy
*Assistant Examiner*—Barbara Badio
*Attorney, Agent, or Firm*—Oblon, Spivak, McClelland, Maier & Neustadt, P.C.

[57] ABSTRACT

Use of aminotriarylmethanes of the formula

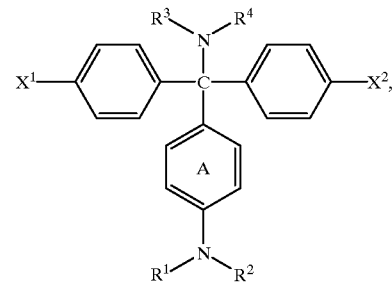

where
  the ring A may be benzofused, and
  $R^1$ and $R^2$ are each substituted or unsubstituted $C_1$–$C_{13}$-alkyl or substituted or unsubstituted phenyl, or $R^1$ and $R^2$ are together with the nitrogen atom joining them together a heterocyclic radical, or else $R^1$ is hydrogen,
  $R^3$ and $R^4$ are substituted or unsubstituted $C_1$–$C_{20}$-alkyl or else $R^3$ is hydrogen, and
  $X^1$ and $X^2$ are each substituted or unsubstituted $C_1$–$C_{13}$-alkyl or a radical of the formula $NR^1R^2$, or else one of $X^1$ and $X^2$ is hydrogen,
for marking hydrocarbons, hydrocarbons comprising the abovementioned aminotriarylmethanes, a method for detecting the aminotriarylmethanes in hydrocarbons, and novel aminotriarylmethanes.

13 Claims, No Drawings

USE OF AMINOTRIARYLMETHANES FOR MARKING HYDROCARBONS AND NOVEL AMINOTRIARYLMETHANES

This application is a 371 of PCT/EP94/01941 filed Jun. 15, 1994.

The present invention relates to the use of aminotriarylmethanes of the formula I

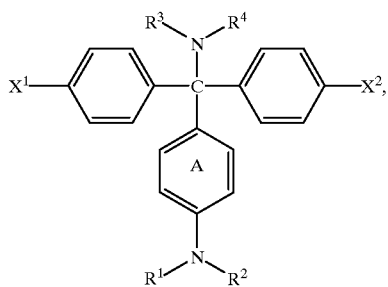

where
the ring A may be benzofused,
$R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen,
$R^3$ and $R^4$ are identical or different and each is independently of the other $C_1$–$C_{20}$-alkyl with or without interruption by from 1 to 4 oxygen atoms in ether function and with or without amino, hydroxyl or phenyl substitution, or else $R^3$ is hydrogen, and
$X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen,
for marking hydrocarbons, hydrocarbons comprising the aminotriarylmethanes of the formula I, a method for detecting the aminotriarylmethanes of the formula I in hydrocarbons, and novel aminotriarylmethanes.

U.S. Pat. No. 5,145,573 discloses the use of triarylmethane dyes or triarylmethanecarbinols for marking mineral oils.

It is an object of the present invention to provide novel markers for hydrocarbons. The novel markers shall be readily obtainable and soluble in hydrocarbons. They shall also be simple to detect; specifically, even very small amounts of marker shall be visibilizable through a strong color reaction.

We have found that this object is achieved by the above-defined aminotriarylmethanes of the formula I.

Any alkyl appearing in the abovementioned formula I may be straight-chain or branched.

Any substituted alkyl appearing in the abovementioned formula I generally has 1 or 2 substituents.

Any substituted phenyl appearing in the abovementioned formula I may have as substituents for example $C_1$–$C_4$-alkyl or $C_1$–$C_4$-alkoxy. The substituents generally number from 1 to 3.

$R^1$ and $R^2$ combined with the nitrogen atom joining them together into a 5- or 6-membered saturated heterocyclic radical with one further hetero atom can be for example pyrrolidinyl, piperidinyl, morpholinyl, piperazinyl or N-($C_1$–$C_4$-alkyl)piperazinyl.

$R^1$, $R^2$, $R^3$, $R^4$, $X^1$ and $X^2$ are each for example methyl, ethyl, propyl, isopropyl, butyl, isobutyl, sec-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above designations isooctyl, isononyl, isodecyl and isotridecyl are trivial names derived from the oxo process alcohols—cf. Ullmann's Encyklopädie der technischen Chemie, 4th edition, Volume 7, pages 215 to 217, and Volume 11, pages 435 and 436), 2-hydroxyethyl, 2- or 3-hydroxypropyl, 2- or 4-hydroxybutyl, 5-hydroxypentyl, 6-hydroxyhexyl, 5-hydroxy-3-oxapentyl, 2-aminoethyl, 2- or 3-aminopropyl, 2- or 4-aminobutyl, 5-aminopentyl, 6-aminohexyl, 7-aminoheptyl, 8-aminooctyl, 5-amino-3-oxapentyl, 6-amino-3-oxahexyl, 6-amino-4-oxahexyl, 7-amino-4-oxaheptyl, 8-amino-3,6-dioxaoctyl, 3-aminoprop-2-yl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxyoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl or 3,6,9-trioxaundecyl.

$R^3$ and $R^4$ may each also be for example tetradecyl, pentadecyl, hexadecyl, heptadecyl, octadecyl, nonadecyl, eicosyl, benzyl, 1- or 2-phenylethyl, 3,6,9-trioxadodecyl, 3,6,9,12-tetraoxatridecyl or 3,6,9,12-tetraoxatetradecyl.

Preference for marking hydrocarbons is given to the use of aminotriarylmethanes of the formula I where $R^1$ and $R^2$ are each independently of the other $C_1$–$C_4$-alkyl or substituted or unsubstituted phenyl, or else $R^1$ is hydrogen.

Preference for marking hydrocarbons is further given to the use of aminotriarylmethanes of the formula I where $R^3$ and $R^4$ are each independently of the other $C_6$–$C_{13}$-alkyl with or without interruption by 1 or 2 oxygen atoms in ether function, or else $R^3$ is hydrogen.

Preference for marking hydrocarbons is further given to the use of aminotriarylmethanes of the formula I where $X^1$ and $X^2$ are each independently of the other $C_1$–$C_4$-alkyl or $C_1$–$C_4$-dialkylamino, or else one of $X^1$ and $X^2$ is hydrogen.

The present invention further provides hydrocarbons comprising one or more of the aminotriarylmethanes of the formula I.

Preference is given to hydrocarbons comprising one or more of the aminotriarylmethanes of the formula I where $R^1$ and $R^2$ are each independently of the other $C_1$–$C_4$-alkyl or substituted or unsubstituted phenyl, or else $R^1$ is hydrogen.

Preference is further given to hydrocarbons comprising one or more of the aminotriarylmethanes of the formula I where $R^3$ and $R^4$ are each independently of the other $C_6$–$C_{13}$-alkyl with or without interruption by 1 or 2 oxygen atoms in ether function, or else $R^3$ is hydrogen.

Preference is further given to hydrocarbons comprising one or more of the aminotriarylmethanes of the formula I where $X^1$ and $X^2$ are each independently of the other $C_1$–$C_4$-alkyl or $C_1$–$C_4$-dialkylamino, or else one of $X^1$ and $X^2$ is hydrogen.

Hydrocarbons for the purposes of the present invention are aliphatic or aromatic hydrocarbons which are liquid under standard conditions. They are in particular mineral oils, for example motor fuels, such as gasoline, kerosine or diesel fuel, or oils, such as heating oil or engine oil.

The aminotriarylmethanes of the formula I are especially suitable for marking mineral oils where some form of marking is mandatory, for example for tax reasons. To keep the costs for this to a minimum, it is desirable to keep the amount of marker used to a minimum.

To mark hydrocarbons, the aminotriarylmethanes of the formula I are used either without a solvent or in the form of solutions. Suitable solvents are organic solvents. Preference is given to using aromatic hydrocarbons, such as toluene, xylene, dodecylbenzene, diisopropylnaphthalene or a mixture of higher aromatics available from Shell as Shellsol® AB. To avoid the resulting solutions having a high viscosity, the concentration of aminotriarylmethane I chosen for the solution generally ranges from 20 to 80% by weight, based on the solution.

The aminotriarylmethanes of the formula I to be used according to the present invention permit very simple detection of marked hydrocarbons, even if the marker is present only in a concentration of about 10 ppm or less.

The presence in hydrocarbons of the aminotriarylmethanes of the formula I used as markers is advantageously detected by treating the mineral oil with an aqueous alcoholic medium comprising a protic acid with or without halide of the metals zinc, aluminum or tin.

The addition of the protic acid, and optionally the metal halide, to the marked hydrocarbon results in a clearly visible color reaction through the formation of a triarylmethane dye, which transfers to the aqueous alcoholic phase.

Suitable alcohols include for example ethanol, propanol or 1-methoxypropan-2-ol. The use of ethanol is preferred.

Suitable protic acids for the method of the present invention include in particular so-called strong acids, ie. protic acids with a $pKa \leq 3.5$. Suitable such acids include for example inorganic or organic acids, such as perchloric acid, hydroiodic acid, hydrochloric acid, hydrobromic acid, hydrofluoric acid, sulfuric acid, nitric acid, phosphoric acid, benzenesulfonic acid, naphthalenesulfonic acid, methanesulfonic acid, oxalic acid, maleic acid, chloroacetic acid, dichloroacetic acid and bromoacetic acid. In some cases it can be of advantage to buffer these acids, for example by adding acetic acid.

Particular emphasis is given to inorganic acids, and hydrochloric acid or sulfuric acid is of particular importance.

Suitable halides of the metals zinc, aluminum or tin include for example zinc chloride, zinc bromide, aluminum chloride, aluminum bromide and tin tetrachloride.

Particular emphasis is given to zinc chloride.

It is generally sufficient to extract about 20 ml of the mineral oil marked according to the present invention with 10 ml of an aqueous alcoholic solution of a protic acid, optionally in the presence of the metal halide, to obtain this color reaction. It is also possible to use an aqueous alcoholic solution of the metal halide alone, since it likewise has an acidic reaction.

The concentration of protic acid in the aqueous alcoholic solution is generally from 5 to 50% by weight, preferably from 10 to 30% by weight. The concentration of metal halide is generally from 10 to 20% by weight and the concentration of alcohol is generally from 10 to 40% by weight.

Preference is given to a method for detecting aminotriarylmethanes of the formula I where $R^1$ and $R^2$ are each independently of the other $C_1$–$C_4$-alkyl or substituted or unsubstituted phenyl, or else $R^1$ is hydrogen.

Preference is further given to a method for detecting aminotriarylmethanes of the formula I where $R^3$ and $R^4$ are each independently of the other $C_6$–$C_{13}$-alkyl with or without interruption by 1 or 2 oxygen atoms in ether function, or else $R^3$ is hydrogen.

Preference is further given to a method for detecting aminotriarylmethanes of the formula I where $X^1$ and $X^2$ are each independently of the other $C_1$–$C_4$-alkyl or $C_1$–$C_4$-dialkylamino, or else one of $X^1$ and $X^2$ is hydrogen.

The present invention further provides aminotriarylmethanes of the formula Ia

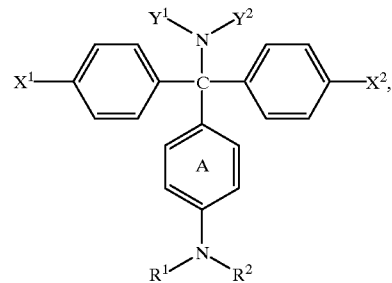

(Ia)

where the ring A may be benzofused, $R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $Y^1$ and $Y^2$ are identical or different and each is independently of the other $C_1$–$C_{20}$-alkyl with or without interruption by from 1 to 4 oxygen atoms in ether function and with or without amino, hydroxyl or phenyl substitution, or else $Y^1$ is hydrogen, and $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen.

For exemplification of the individual radicals in the formula Ia, reference is made to the earlier observations.

Preference is given to aminotriarylmethanes of the formula Ia, where $R^1$ and $R^2$ are each independently of the other $C_1$–$C_4$-alkyl or substituted or unsubstituted phenyl, or else $R^1$ is hydrogen.

Preference is further given to aminotriarylmethanes of the formula Ia where $Y^1$ and $Y^2$ are each independently of the other $C_6$–$C_{13}$-alkyl with or without interruption by 1 or 2 oxygen atoms in ether function, or else $Y^1$ is hydrogen.

Preference is further given to aminotriarylmethanes of the formula Ia where $X^1$ and $X^2$ are each independently of the other $C_1$–$C_4$-alkyl or $C_1$–$C_4$-dialkylamino, or else one of $X^1$ and $X^2$ is hydrogen.

The novel aminotriarylmethanes of the formula Ia as well as the other aminotriarylmethanes of the formula I known from EP-A-433 813 are obtainable in a conventional manner, for example as described in EP-A-433 813.

For example, a triarylmethane base of the formula II

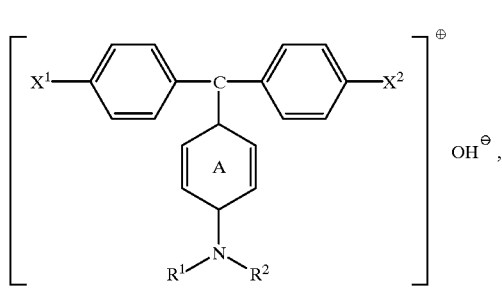

(II)

where $R^1$, $R^2$, $X^1$, $X^2$ and the ring A are each as defined above, can be reacted with an amine of the formula IIIa or IIIb

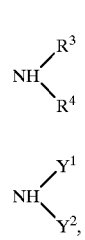

(IIIa)

(IIIb)

where $R^3$, $R^4$, $Y^1$ and $Y^2$ are each as defined above.

The novel aminotriarylmethanes of the formula Ia are readily soluble in organic solvents and, as mentioned earlier, are advantageously suitable for marking hydrocarbons.

The Examples which follow illustrate the invention.

EXAMPLE 1

A) Preparation 14.2 g of ethylviolet base of the formula

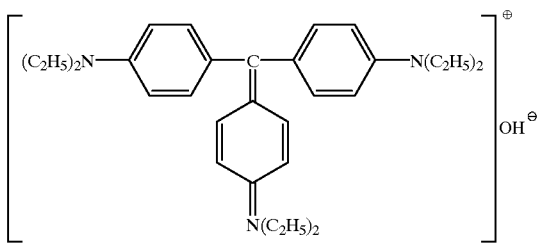

and 4 g of 3-(2-ethylhexyloxy)propylamine were refluxed in 100 ml of toluene for 7 h. After cooling down, the reaction mixture was washed with water and dried over sodium sulfate. Removal of the solvent left 16.9 g of a compound of the formula

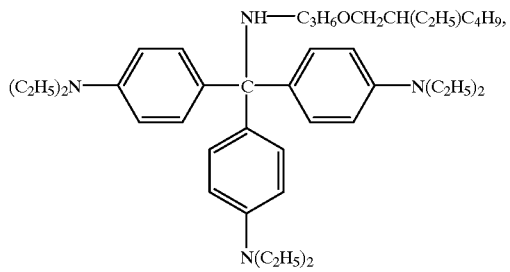

[$\lambda_{max}$ (in acetic acid): 587 nm]

which still contained about 10% of starting material as by-product.

The same method gives the aminotriarylmethanes of the formula

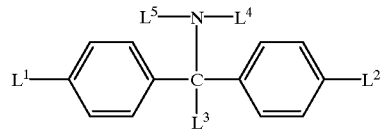

listed in the table below:

| Ex. No. | $L^1$ | $L^2$ | $L^3$ | 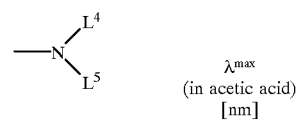 | $\lambda^{max}$ (in acetic acid) [nm] |
|---|---|---|---|---|---|
| 2 | $N(C_2H_5)_2$ | $N(C_2H_5)_2$ | —⟨⟩—$N(C_2H_5)_2$ | 3-(2-Methoxy-ethoxy)propylamino | 587 |
| 3 | $N(C_2H_5)_2$ | $N(C_2H_5)_2$ | —⟨⟩—$N(C_2H_5)_2$ | 2-Ethylhexylamino | 578 |

-continued

| Ex. No. | L¹ | L² | L³ | —N(L⁴)(L⁵) | $\lambda^{max}$ (in acetic acid) [nm] |
|---|---|---|---|---|---|
| 4 | N(C₂H₅)₂ | N(C₂H₅)₂ |  | 3-(2-Methoxy-ethoxy)propylamino | 613 |
| 5 | N(C₂H₃)₂ | N(C₂H₃)₂ | 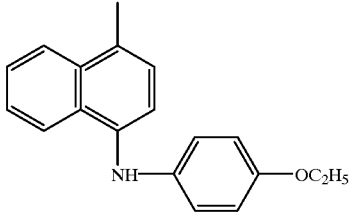 | 3-(2-Methoxy-ethoxy)propylamino | 591 |
| 6 | N(C₂H₃)₂ | N(C₂H₃)₂ | 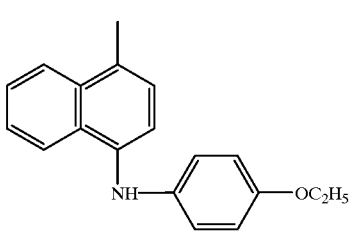 | 3-(2-Methoxy-ethoxy)propylamino | 589 |
| 7 | H | N(C₂H₅)₂ | 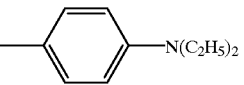 | 3-(2-Ethylhexyl-oxy)propylamino | 627 |
| 8 | H | N(C₂H₅)₂ | 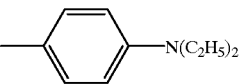 | 3-(2-Methoxy-ethoxy)propylamino | 627 |
| 9 | H | N(C₂H₅)₂ | 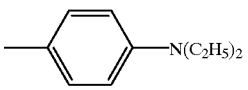 | 3-(4-Hydroxy-butoxy)propylamino | 627 |
| 10 | H | N(C₂H₅)₂ | 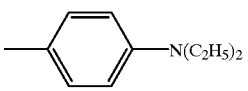 | Isopentylamino | 626 |
| 11 | H | N(C₂H₅)₂ | 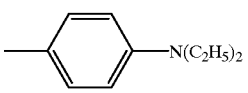 | 10-Amino-4,7-dioxadecylamino | 627 |
| 12 | H | N(C₂H₅)₂ | 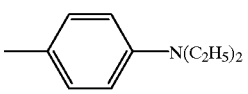 | Bis(2-ethylhexyl)-amino | 626 |

B) Application

General Method

Commercial diesel fuel is admixed with a 40% strength by weight solution of the marker in a commercial mixture of higher aromatics—Shellsol® AB (from Shell).

The amount of marker added is 10 ppm.

20 ml of marked diesel fuel are vigorously shaken up with 20 ml of the reagent solution (10% strength by weight zinc chloride solution in 60:40 v/v water/ethanol, pH adjusted to 2 by addition of 85% strength by weight acetic acid). The lower, aqueous phase takes on a distinct color. The aqueous phase can be measured photometrically against a solution of known concentration.

The above-listed markers (Examples 1 to 12) each gave similar results.

We claim:

1. A method of marking hydrocarbons comprising adding to a hydrocarbon a marking substance which is an aminotriarylmethane of the formula I

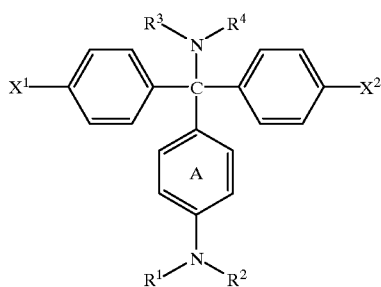

where the ring A may be benzofused,

R₁ and R² are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $R^3$ and $R^4$ are identical or different and each is independently of the other $C_1$–$C_{20}$-alkyl with or without interruption by from 1 to 4 oxygen atoms in ether function with or without phenyl substitution, and with amino or hydroxyl substitution or else $R^3$ is hydrogen and $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen.

2. The method of claim 1, wherefor $R^1$ and $R^2$ are each independently of the other $C_1$–$C_4$-alkyl or substituted or unsubstituted phenyl, or else $R^1$ is hydrogen.

3. The method of claim 1, wherefor $R^3$ and $R^4$ are each independently of the other $C_6$–$C_{13}$-alkyl with or without interruption by 1 or 2 oxygen atoms in ether function, with amino or hydroxyl substitution or else $R^3$ is hydrogen.

4. The method of claim 1, wherefor $X^1$ and $X^2$ are each independently of the other $C_1$–$C_4$-alkyl or $C_1$–$C_4$-dialkylamino, or else one of $X^1$ and $X^2$ is hydrogen.

5. A composition comprising a hydrocarbon and one or more aminotriarylmethanes of the formula I as set forth in claim 1.

6. A method for detecting the presence of aminotriarylmethanes of the formula I

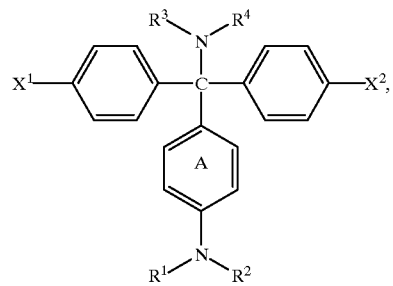

where the ring A may be benzofused, $R^1$ and $R^2$ are identical or different and each is independent of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $R^3$ and $R^4$ are identical or different and each is independently of the other $C_1$–$C_{20}$-alkyl with or without interruption by from 1 to 4 oxygen atoms in ether function, with or without phenyl substitution, and with amino or hydroxyl substitution, or else $R^3$ is hydrogen, and $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen, in hydrocarbons, which comprises treating the hydrocarbon with an aqueous alcoholic medium comprising a protic acid with or without a halide of the metals zinc, aluminum or tin.

7. Aminotriarylmethane of the formula Ia

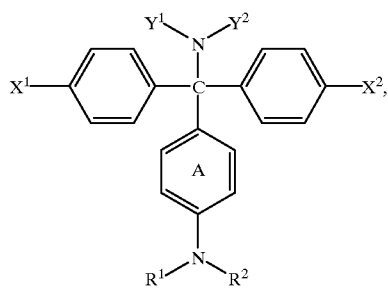

where the ring A may be benzofused, $R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $Y^1$ and $Y^2$ are identical or different and each is independently of the other $C_1$–$C_{20}$-alkyl with or without interruption by from 1 to 4 oxygen atoms in ether function, with or without phenyl substitution, and with amino or hydroxyl substitution, or else $Y^1$ is hydrogen, and $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, wherein $R^1$ and $R^2$ are each as defined above, or else one of $X^1$ and $X^2$ is hydrogen.

8. A method of marking hydrocarbons comprising adding to a hydrocarbon a marking substance which is an aminotriarylmethane of the formula I

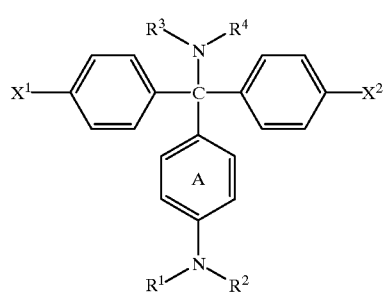

(I)

where the ring A may be benzofused, $R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen, and —$N(R^3)(R^4)$ is selected from the group consisting of —NH—$C_3H_6OCH_2CH(C_2H_5)C_4H_9$— and NH—$C_3H_6OC_2H_4OCH_3$—.

9. A method of marking hydrocarbons comprising adding to a hydrocarbon a marking substance which is an aminotriarylmethane of the formula I

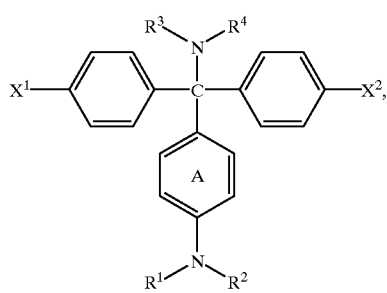

where the ring A is benzofused, $R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $R^3$ and $R^4$ are identical or different and each is independently of the other $C_1$–$C_{20}$-alkyl with or without interruption by from 1 to 4 oxygen atoms in ether function, and with or without amino, hydroxyl or phenyl substitution, or else $R^3$ is hydrogen, and $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen.

10. A method for detecting the presence of aminotriarylmethanes of the formula I

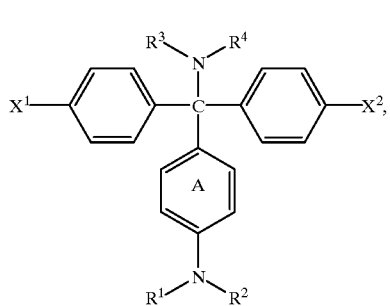

(I)

where the ring A may be benzofused, $R^1$ and $R^2$ are identical or different and each is independent of the other $C_{1-13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen, $X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen, and —$N(R^3)(R^4)$ is selected from the group consisting of —NH—$C_3H_6OCH_2CH(C_2H_5)C_4H_9$— and NH—$C_3H_6OC_2H_4OCH_3$—, in hydrocarbons, which comprises treating the hydrocarbon with an aqueous alcoholic medium comprising a protic acid with or without a halide of the metals zinc, aluminum or tin.

11. A method for detecting the presence of aminotriarylmethanes of the formula I (I)

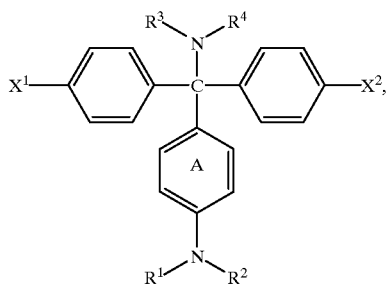

where
the ring A is benzofused,
$R^1$ and $R^2$ are identical or different and each is independently of the other $C_{1-3}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen,
$R^3$ and $R^4$ are identical or different and each is independently of the other $C_1$–$C_{20}$-alkyl with or without interruption by from 1 to 4 oxygen atoms in ether function, and with or without amino, hydroxyl or phenyl substitution, or else $R^3$ is hydrogen, and
$X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen, in hydrocarbons, which comprises treating the hydrocarbon with an aqueous alcoholic medium comprising a protic acid with or without a halide of the metals zinc, aluminum or tin.

12. Aminotriarylmethane of the formula Ia (Ia)

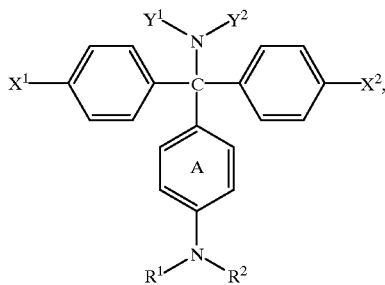

where the ring A may be benzofused,
$R^1$ and $R^2$ are identical or different and each is independently of the other $C_{1-3}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen,
$X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen, and
—$N(Y^1)(Y^2)$ is selected from the group consisting of —NH—$C_3H_6OCH_2CH(C_2H_5)C_4H_9$— and NH—$C_3H_6OC_2H4OCH_3$—.

13. Aminotriarylmethane of the formula Ia (Ia)

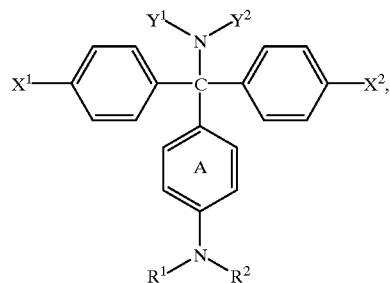

where the ring A is benzofused,
$R^1$ and $R^2$ are identical or different and each is independently of the other $C_1$–$C_{13}$-alkyl with or without interruption by from 1 to 3 oxygen atoms in ether function and with or without amino or hydroxyl substitution, or substituted or unsubstituted phenyl, or $R^1$ and $R^2$ are together with the nitrogen atom joining them together a 5- or 6-membered saturated heterocyclic radical with or without a further heteroatom, or else $R^1$ is hydrogen,
$Y^1$ and $Y^2$ are identical or different and each is independently of the other $C_{1-C20}$-alkyl with or without interruption by from 1 to 4 oxygen atoms in ether function, and with or without amino, hydroxyl or phenyl substitution, or else $Y^1$ is hydrogen, and
$X^1$ and $X^2$ are identical or different and each is independently of the other $C_1$–$C_{13}$-alkyl with or without interruption by from 1 to 3 oxygen atoms in ether function and with or without amino or hydroxyl substitution, or a radical of the formula $NR^1R^2$, where $R^1$ and $R^2$ are each as defined above, or else one of $X^1$ and $X^2$ is hydrogen.

* * * * *